United States Patent
Fitzgerald et al.

(10) Patent No.: US 10,904,646 B2
(45) Date of Patent: Jan. 26, 2021

(54) MOVEMENT SENSING APPARATUS FOR USE IN A FOOTWEAR ITEM

(71) Applicant: Plantiga Technologies Inc., Vancouver (CA)

(72) Inventors: Colin Edward Fitzgerald, Kimberley (CA); Quin Samuel McKay Sandler, Vancouver (CA)

(73) Assignee: Plantiga Technologies Inc., Vancouver (CA)

( * ) Notice: Subject to any disclaimer, the term of this patent is extended or adjusted under 35 U.S.C. 154(b) by 0 days.

(21) Appl. No.: 16/495,384

(22) PCT Filed: Mar. 23, 2018

(86) PCT No.: PCT/CA2018/000062
§ 371 (c)(1),
(2) Date: Sep. 18, 2019

(87) PCT Pub. No.: WO2018/170581
PCT Pub. Date: Sep. 27, 2018

(65) Prior Publication Data
US 2020/0021896 A1 Jan. 16, 2020

Related U.S. Application Data

(60) Provisional application No. 62/634,315, filed on Feb. 23, 2018, provisional application No. 62/475,859, filed on Mar. 23, 2017.

(51) Int. Cl.
*A43B 3/00* (2006.01)
*H04Q 9/00* (2006.01)
(Continued)

(52) U.S. Cl.
CPC ............ *H04Q 9/00* (2013.01); *A43B 3/0005* (2013.01); *G01P 13/00* (2013.01); *H04W 4/38* (2018.02);
(Continued)

(58) Field of Classification Search
None
See application file for complete search history.

(56) References Cited

U.S. PATENT DOCUMENTS

| | | | |
|---|---|---|---|
| 2006/0143645 A1* | 6/2006 | Vock | A43B 3/00 725/9 |
| 2009/0137933 A1* | 5/2009 | Lieberman | A61B 5/1036 600/595 |

(Continued)

OTHER PUBLICATIONS

International Search Report and Written Opinion issued by the International Searching Authority in relation to corresponding International Application No. PCT/CA2018/000062 dated May 29, 2018, 8 pgs.

(Continued)

*Primary Examiner* — Curtis A Kuntz
*Assistant Examiner* — Jerold B Murphy
(74) *Attorney, Agent, or Firm* — Voyer Law

(57) ABSTRACT

A movement sensing apparatus for use in a footwear item worn on a test subject, such as a person. The apparatus has movement sensor(s), an embedded electrical circuit, and an energy source. The sensor(s) generate movement signals representing movement of the footwear item while worn on a test subject's foot. The electrical circuit has a processor circuit coupled to receive the movement signals from the sensor(s), a buffer memory in communication with the processor circuit for storing movement data representing the movement signals, and a wireless interface controlled by the processor circuit for wirelessly transmitting movement data to an external host computing platform via an antenna. The energy source provides power to the circuit and sensor(s).

22 Claims, 4 Drawing Sheets

(51) Int. Cl.
 *H04W 4/38* (2018.01)
 *G01P 13/00* (2006.01)
(52) U.S. Cl.
 CPC ..... *H04Q 2209/43* (2013.01); *H04Q 2209/82* (2013.01); *H04Q 2209/886* (2013.01)

(56) References Cited

U.S. PATENT DOCUMENTS

| | | | |
|---|---|---|---|
| 2010/0063779 A1* | 3/2010 | Schrock | A43B 3/00 702/188 |
| 2013/0213145 A1 | 8/2013 | Owings et al. | |
| 2015/0048942 A1* | 2/2015 | Bertagna | G08B 21/0291 340/539.13 |
| 2015/0257679 A1 | 9/2015 | Ross | |
| 2017/0135444 A1* | 5/2017 | Vincent | G08C 17/02 |
| 2017/0188950 A1* | 7/2017 | Gazdag | A61B 5/6807 |
| 2017/0249417 A1* | 8/2017 | Gosieski, Jr. | G06F 30/17 |

OTHER PUBLICATIONS

Hedge et al., "SmartStep 2.0—A completely wireless, versatile insole monitoring system", Bioinformatics and Biomedicine (BIBM), IEEE International Conference, Dec. 17, 2015, *Abstract, p. 746, col. 2-748-col. 1, p. 749 col. 1, figs 1 and 2.

* cited by examiner

MOVEMENT SENSING APPARATUS FOR USE IN A FOOTWEAR ITEM

RELATED APPLICATIONS

This application claims the benefit of provisional patent application U.S. 62/475,859 entitled "Compact Under-Foot Device that Measures the Motion of Each Part of the Foot", filed on Mar. 23, 2017 and incorporated herein by reference in its entirety.

This application claims the benefit of provisional patent application U.S. 62/634,315 entitled "Apparatus for Charging an Energy Storage Element in a Shoe used in Movement Testing and a Kiosk System for Administering a Movement Test", filed on Feb. 23, 2018 and incorporated herein by reference in its entirety.

BACKGROUND

1. Field

This disclosure relates generally to human motion analysis and more particularly to a movement sensing apparatus for use in a footwear item.

2. Description of Related Art

Force plates and video based motion capture systems are commonly used to measure human motion patterns with a view to determine whether irregularities such as asymmetry of movement are present that could lead to injury. Laboratory based capture systems may be used to provide adequate frequency of data reporting, but such systems are constrained to operation in a test environment and may not accurately replicate real-world conditions such as on a sports field or athletic track.

Many other motion capture systems suffer from a lack of adequate sensor resolution, have a limited bandwidth for transferring data, and thus may not provide sufficiently accurate movement data to fully characterize the test subject's movement. Some solutions require the use of bulky auxiliary equipment worn on the test subjects body and thus may impede normal motion. Other solutions are unable to capture data in real time, requiring downloading of data following completion of the movement test. Another problem encountered is in the limited range associated with wireless transmission of movement data between sensors and a host platform. There remains a need for improved movement sensing apparatus and methods.

SUMMARY

In accordance with one disclosed aspect there is provided a movement sensing apparatus for use in a footwear item. The apparatus includes at least one movement sensor operable to generate movement signals representing movement of the footwear item while being worn on a test subject's foot. The apparatus also includes an embedded electrical circuit including a processor circuit coupled to receive the movement signals from the at least one movement sensor, a buffer memory in communication with the processor circuit for storing movement data representing the movement signals, and a wireless interface controlled by the processor circuit an operably configured to wirelessly transmit movement data to an external host computing platform via an antenna. The apparatus also includes an energy source operable to provide operating power to the embedded electrical circuit and movement sensor. The processor circuit is operably configured to inhibit transmission by the wireless interface while accumulating movement data in the buffer memory, and transmit movement data from the buffer memory to the host computing platform in a burst transmission when the accumulated movement data in the buffer memory reaches a transmission threshold.

The wireless interface may be operably configured to implement an IEEE 802.11 transmission protocol.

The wireless interface may be further operably configured to implement a Bluetooth transmission protocol and wherein the burst transmission is transmitted to the host computing platform using the IEEE 802.11 transmission protocol, and other operational data is transmitted between the host computing platform and the movement sensing apparatus using the Bluetooth transmission protocol.

The other operational data may include at least one of commands issued by the host computing platform to the movement sensing apparatus, status data representing a state of the movement sensing apparatus transmitted to the host computing platform, and program codes downloaded from the host computing platform to a program memory in communication with the processor circuit for configuring movement test functionality of the movement sensing apparatus.

The antenna may be disposed under a lateral instep portion of the test subject's foot.

The embedded electrical circuit may be disposed below an instep portion of the test subject's foot.

The energy storage element may be disposed below an instep portion of the test subject's foot.

The apparatus may include a strain plate disposed over at least one of the embedded electrical circuit, the movement sensor, and the energy source and the strain plate being operably configured to redirect forces exerted by the test subject's foot away from the embedded electrical circuit, movement sensor, or the energy source.

The strain plate may be operably configured to cover both the embedded electrical circuit and the energy source.

Each strain plate may include an upper plate disposed above the at least one of the embedded electrical circuit, the movement sensor, and the energy source and a lower plate disposed below the at least one of the embedded electrical circuit, the movement sensor, and the energy source.

At least one of the upper and lower plates may include a concave inner surface and the upper and lower plates may be operably configured to engage at a peripheral edge providing an interior volume for accommodating the at least one of the embedded electrical circuit, the movement sensor, and the energy source such that forces imparted on the at least one of the upper and lower plates by the test subject's foot are redirected to the peripheral edge.

The strain plate may include one of a carbon fiber plate and a steel plate.

The strain plate may have a thickness of about 0.7 mm.

The movement sensor may include a plurality of inertial movement sensors, at least one sensor being located in a heel region of the footwear item and at least one sensor being located in a toe region of the footwear item, each sensor being connected to the processor circuit via a flexible and stretchable interconnect.

The movement sensor apparatus may be accommodated on a flexible substrate and the flexible interconnect may include a conductive material printed onto the flexible substrate.

The energy source may include a battery capable of dynamically flexing in response to movement of the test subject's foot.

The apparatus may include an induction coil operably configured to receive an externally applied alternating magnetic field and to generate a charging current for charging the energy source.

A host computing platform may be operably configured to receive the burst transmission of movement data from the movement sensing apparatus.

The host computing platform may include a plurality of wireless access points spaced apart within a test region and being operable to receive the burst transmission.

The movement sensing apparatus may be further configured to transmit movement data from the buffer memory to the host computing platform in a burst transmission when the movement sensing apparatus is in wireless transmission range of one of the plurality of wireless access points.

The movement sensing apparatus may be embedded within a removable insole inserted into the footwear item.

The processor circuit may be operably configured to pre-process the movement data prior to storing the movement data in the buffer memory and the pre-processing may include at least one of compressing the data and encrypting the data.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
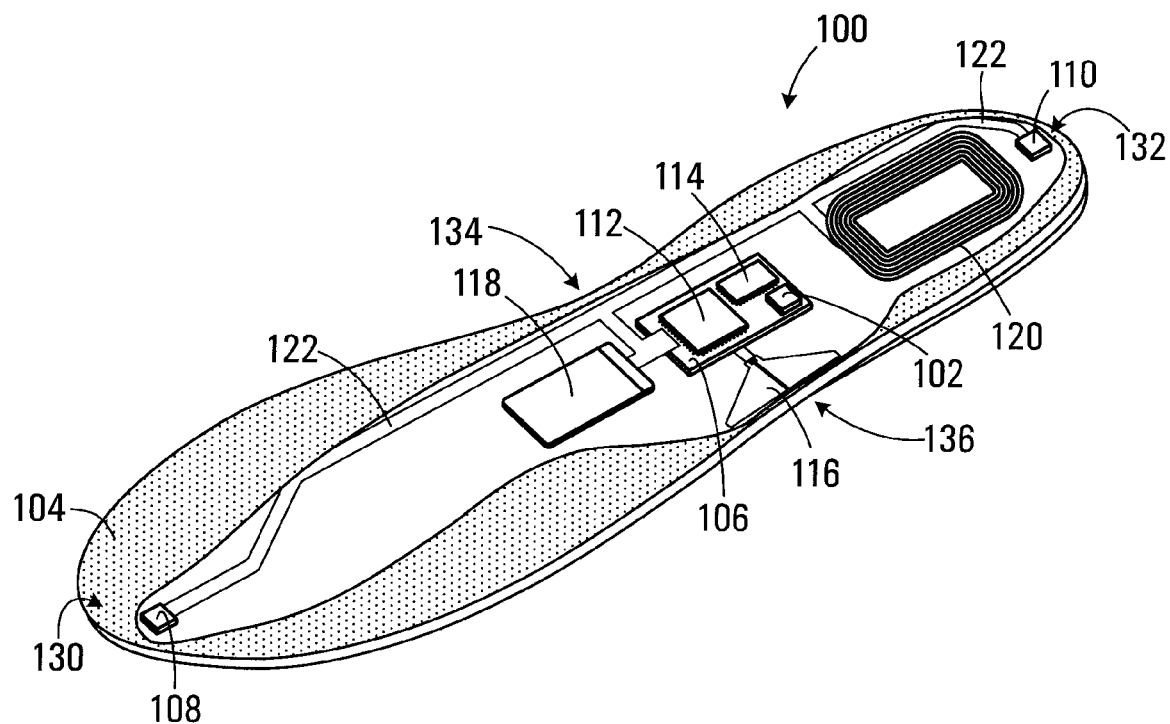
FIG. 1 is a perspective view of a movement sensing apparatus in accordance with one disclosed embodiment.
Figure 2:
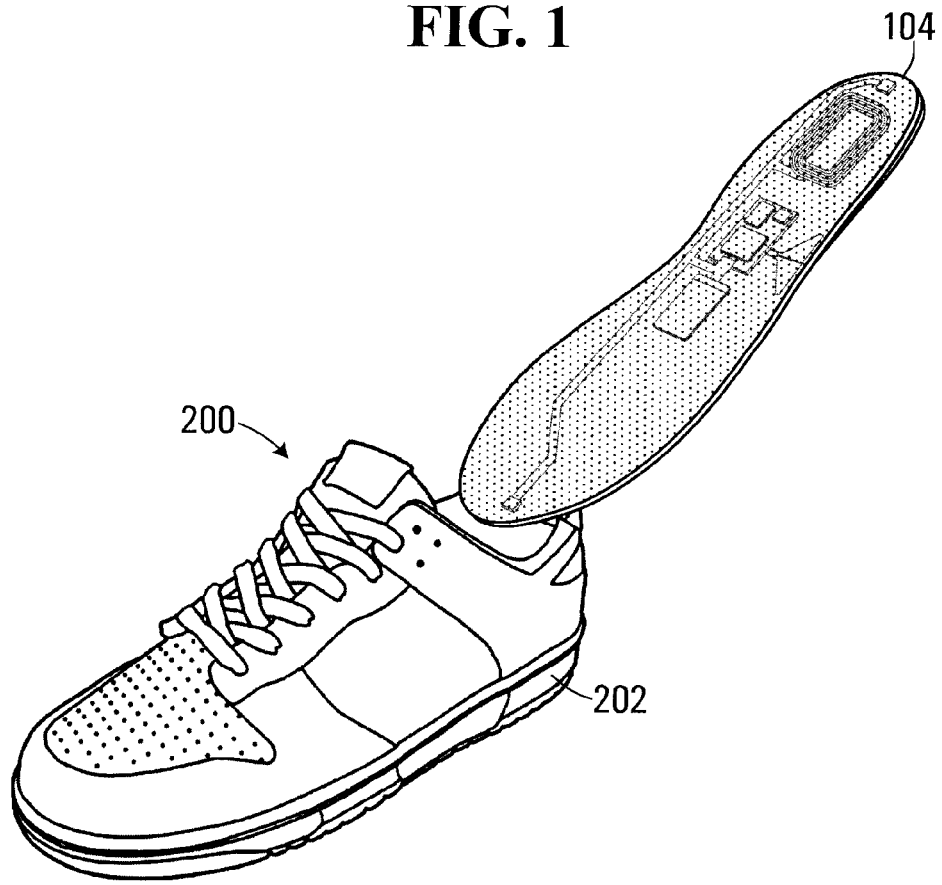
FIG. 2 is a perspective view of the movement sensing apparatus of FIG. 1 being inserted into a footwear item.

Referring to FIG. 1, a movement sensing apparatus for use in a footwear item in accordance with one disclosed embodiment is shown generally at 100. In the embodiment shown the movement sensing apparatus 100 is embedded within an insole 104, which is inserted into a footwear item 200 as shown in FIG. 2. In other embodiments the movement sensing apparatus 100 may be embedded within a sole 202 of the footwear item 200 or the apparatus may be included in a shoe, boot, slipper, sock, or any other kind of footwear. While only a left insole 104 and left footwear item 200 are shown in FIG. 1 and FIG. 2, the apparatus may be included in both the left and right footwear items to provide movement sensing for each of the test subject's feet individually. The movement sensing apparatus 100 shown in FIG. 1 would be similarly configured for the right footwear item, except that the layout may be mirrored to match the anatomy of the test subject's foot.

The apparatus 100 includes at least one movement sensor 102, which is operable to generate movement signals representing movement of the footwear item 200 while being worn on a test subject's foot. In the embodiment shown the movement sensor 102 is located on an embedded electrical circuit 106, however the movement sensing apparatus 100 may include additional movement sensors, such as the movement sensor 108 located at a toe portion 130 of the insole 104 and the movement sensor 110 located at a heel portion 132 of the insole. Further movement sensors (not shown) may be located at other locations on the insole 104, for example at a medial instep portion 134 and/or a lateral instep portion 136 of the insole 104. The additional sensors provide movement data associated with specific portions of the foot and may facilitate detection of specific patterns of movement providing an insight into the test subject's biomechanics. Some embodiments may omit the movement sensors 108 and 110 and have only the movement sensor 102 located on the embedded electrical circuit 106. In other embodiments the sensor 102 on the embedded electrical circuit 106 may be omitted in favor of sensors located elsewhere on the insole 104.

In one embodiment the movement sensors 102, 108 and 110 may be implemented using an MPU-9250 motion tracking device manufactured by InvenSense of San Jose Calif. The MPU-9250 is a low power sensing device in a 3 mm×3 mm×1 mm package and includes a 3 axis accelerometer, a 3 axis gyroscope, a 3 axis magnetometer, and an onboard processor. In other embodiments alternative movement sensors may be included, such as a pressure transducer that measures a foot strike pressure or a temperature sensor that measures a temperature of the test subject's foot within the footwear item.

The implemented sensors on the movement sensing apparatus 100, by sensing movement of the test subject's feet, also facilitates determination of movement information related to the whole body of the test subject. For example, analyzing foot strike and toe-off patterns provides data that allows assessment of the gait of the test subject, possibly revealing imbalances and/or other issues with the test subject's kinetic chain during movement that may result in performance issues.

The embedded electrical circuit 106 also includes a processor circuit 112 coupled to receive the movement signals from the movement sensor 102. The processor circuit 112 may be implemented using the ESP32 processor manufactured by Espressif Systems of Shanghai, China, which is a low power microprocessor specifically configured for Internet of things (IoT) applications.

The embedded electrical circuit 106 also includes a buffer memory 114 in communication with the processor circuit 112, which provides a memory for storing movement data representing the movement signals. In one embodiment the buffer memory 114 may be a non-volatile storage medium such as a flash memory but in other embodiments a volatile memory that requires electrical power for operation may also be used. In one embodiment the embedded electrical circuit 106 is constructed on a printed circuit board (PCB)

and the buffer memory 114 is implemented using a 1 GBit NAND flash chip suitable for mounting on a PCB. In other embodiments the buffer memory 114 may be implemented using a removable memory such as a SD non-volatile memory card that facilitates removal for analysis of stored movement data on another computing platform.

The processor circuit 112 may also include on-chip memory storage for storing boot and program codes for configuring the processor circuit 112 to perform functions for monitoring movement of the test subject. Additionally, the processor circuit 112 may include a small amount of data memory that can be used as a temporary data store. In other embodiments where the processor circuit has sufficient on-chip memory for storage of movement data, the buffer memory 114 may be provided by the on-chip memory.

The embedded electrical circuit 106 further includes a wireless interface controlled by the processor circuit an operably configured to wirelessly transmit movement data to an external host computing platform (not shown) via an antenna 116. The ESP32 processor combines processor functions with an on-chip Wi-Fi and Bluetooth capability, for transmitting and receiving via the antenna 116. In one embodiment a frequency of 2.4 GHz is used for transmission and receiving and the antenna 116 is configured as a dipole antenna suitable for operation at this frequency. In the embodiment shown the antenna 116 is located on the insole 104 such that it will be disposed under a lateral instep portion of the test subject's foot. Under these conditions the antenna 116 was found to have relatively low wireless transmission loss due to the presence of the test subject's foot located in fairly close proximity to the antenna. It was discovered that interaction with the test subject's foot causes some significant attenuation to wireless signals transmitted or received, particularly when located inwardly with respect to the periphery of the insole 104. Other embodiments may employ a ceramic chip antenna or other antenna technology. The embedded electrical circuit 106 is located on the insole 104 such that it will be disposed below an instep or arch portion of the test subject's foot, thus exerting less force on the embedded electrical circuit during movement.

The movement sensing apparatus 100 also includes an energy source 118 for providing operating power to the embedded electrical circuit 106 and movement sensors 102, 108 and 110. The energy source 118 may be a storage device such as a battery, supercapacitor, aerogel based battery or other power source. In the embodiment shown the energy source 118 is implemented as a thin lithium polymer battery having a capacity of about 200 mAH. The energy source 118 may also be disposed below an instep portion of the test subject's foot (i.e. a midfoot portion between the toe and heel portions of the foot) where it will be subjected to reduced forces during movement of the test subject. The toe and heel portions of the foot are generally associated with significantly higher ground contact forces during movement. In one embodiment the energy source 118 may be implemented using a battery capable of dynamically flexing in response to movement of the test subject's foot. While typical thin lithium polymer batteries are capable of withstanding some flexing, repetitive sustained flexing may eventually cause failure of the battery. A battery capable of dynamically flexing may thus extend the service life of the movement sensing apparatus 100 in some embodiments where flexing of the battery occurs. Flexible Lithium batteries are being developed by several manufactures including ProLogium Technology of Taiwan and Brightvolt of WA, United States.

In the embodiment shown, the movement sensing apparatus 100 further includes an induction coil 120 located in a heel portion of the insole 104. The induction coil 120 is operably configured to receive an externally applied alternating magnetic field and to generate a charging current for charging the energy source 118. The induction coil 120 generates an alternating current that may be rectified and regulated to provide a charging current suitable for charging the energy source 118. The induction coil 120 may be configured for any wireless charging configuration such as the Wireless Power Consortium Qi standard, the AirFuel Resonant standard or other proprietary solutions such as provided by NuCurrent of Chicago, Ill. The embedded electrical circuit 106 may further include charging circuitry for charging of the energy source 118. In other embodiments the induction coil 120 may be omitted and the movement sensing apparatus 100 provided with a charging port (not shown) for receiving an externally generated charge current for charging the energy source 118.

Figure 3:
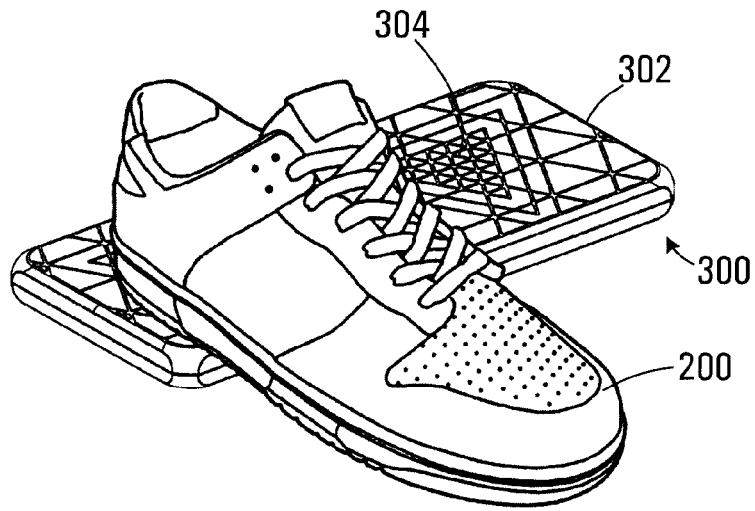
FIG. 3 is a perspective view of a footwear item being wirelessly charged in accordance with a disclosed embodiment.

The alternating magnetic field for charging the energy source 118 may be generated by a wireless charging device, such as disclosed in commonly owned U.S. provisional patent application 62/634,315 entitled "Apparatus for Charging an Energy Storage Element in a Shoe used in Movement Testing and a Kiosk System for Administering a Movement Test", filed on Feb. 23, 2018 and incorporated herein by reference in its entirety. Referring to FIG. 3, the charging apparatus is shown at 300 in FIG. 3 and includes a housing 302 enclosing an electrical circuit (not shown) for generating the alternating magnetic field. The charging apparatus 300 has an upper surface 304 for accommodating heel portions of a pair of footwear items (only one footwear item is shown in FIG. 3). The footwear item 200 is placed on the charging apparatus 300 with a heel portion in contact with the upper surface 304 when charging of the energy source 118 is required.

Referring back to FIG. 1, the movement sensing apparatus 100 also includes a flexible interconnect 122 running though the insole 104 and connecting the movement sensor 110 in the heel region the movement sensor 108 located in the toe region of the footwear item to the processor circuit 112. The flexible interconnect 122 may be subjected to repetitive stresses during movement of the test subject's foot and should be sufficiently flexible and stretchable to maintain the connection in use. In one embodiment the movement sensors 108 and 110 may be mounted on a flexible substrate within the insole 104 and the flexible interconnect may be provided by printing a flexible and stretchable conductive material onto the substrate. The printing may be performed by an inkjet printer or other application method. Other components of the movement sensing apparatus 100 such as the embedded electrical circuit 106, energy source 118, and induction coil 120 may also be connected to each other via the flexible interconnect 122. The movement sensors 108 and 110 when implemented using the MPU-9250 motion tracking device each have 8 connections for providing power, control signals, and data transmission to and from the sensors, although some of the signal and power lines may be shared between sensors. The flexible interconnect 122 would thus need to include a sufficient number of signal and power lines to connect all of these sensors back to the embedded electrical circuit 106 and processor circuit 112.

The electrical components of the movement sensing apparatus 100 may be encapsulated in a flexible matrix. Any of a variety of materials or combinations of materials may be used to produce the insole 104 such as thermoplastic polyurethane (TPU), Poron gel and/or urethanes, silicones, fabric layers, and other commonly used materials for constructing insoles. The insole 104 may include several different materials in layers to provide the necessary support, ergonomics, and hygienic properties required of an insole. The encapsulation of the movement sensing apparatus 100 may be accomplished by molding and/or laminating in layers or any other common manufacturing processes. In some embodiments materials may be selected and applied to the movement sensing apparatus 100 to provide a water resistant encapsulation of the electrical components. For example, the electrical components may be encapsulated in a silicone material. Similar and additional manufacturing techniques may be employed for embodiments where the movement sensing apparatus 100 is disposed within the sole 202 of the footwear item 200.

Figure 4:
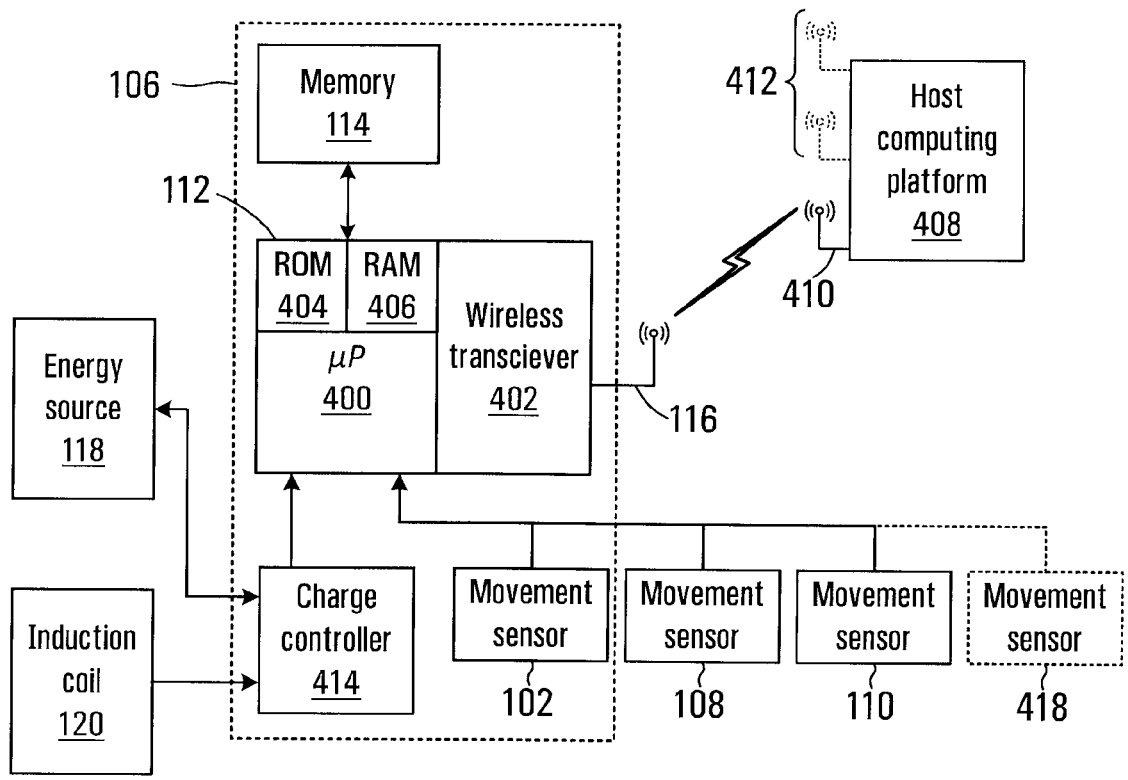
FIG. 4 is a block diagram of electrical components of the movement sensing apparatus shown in FIG. 1.

The embedded electrical circuit 106 and other electrical components of the movement sensing apparatus 100 are shown as a block diagram in FIG. 4. Referring to FIG. 4, the processor circuit 112 includes a microprocessor 400 and a wireless interface 402. For implementations using the Espressif ESP32 processor circuit, the wireless interface 402 is housed on the same semiconductor package as the microprocessor 400. In other embodiments the wireless interface 402 may be separately packaged and mounted on the embedded electrical circuit 106. The microprocessor 400 may have a small amount of on-chip memory, which for the example of the ESP32 microprocessor device includes 448 kB of read only memory (ROM 404) and 520 kB of random access memory (RAM 406).

The wireless interface 402 implements both an IEEE 802.11 Wi-Fi and Bluetooth protocols and is capable of making a connection to a host computing platform 408 using either protocol. In other embodiments, the wireless interface 402 may implement only one of these protocols or may implement another wireless protocol such as ANT+wireless protocol, cellular data transmission protocols, or LiFi (transmission via light modulation). The microprocessor 400 is directed by the program codes stored in the ROM 404 to cause the wireless interface 402 to be selectively configured for transmission of movement data and receiving of other operational data and commands from the host computing platform 408.

The host computing platform 408 is separate and independent from the movement sensing apparatus 100 and is configured to receive movement data from the movement sensing apparatus and to further process the data to generate test results. Various methods may be used to analyze the movement data and a plurality of movement related metrics may be generated providing various insights into the test subject's gait and biomechanics. In some embodiments analysis of the movement data may be performed on the host computing platform 408 and the results displayed of made available to the test subject on a display (not shown) associated with the host or via a web page that can be accessed by the test subject from any connected computing device. Alternatively, the movement data may be transmitted to a networked computing resource via a network connection and the analysis may be performed on the networked computing resource as disclosed in commonly owned provisional patent application U.S. 62/634,315 entitled "Apparatus for Charging an Energy Storage Element in a Shoe used in Movement Testing and a Kiosk System for Administering a Movement Test", filed on Feb. 23, 2018 and which is incorporated herein by reference in its entirety.

The host computing platform 408 includes a wireless access point (WAP) 410 for local communication with the wireless interface 402. In movement tests where the test subject will remain in range of the wireless access point 410, such as in a gymnasium, a single WAP may be sufficient. For movement tests where the test subject will move over a wider area such as a sports field or track, the host computing platform 408 may be connected to receive data from a plurality of additional access points 412 distributed to cover the area within which movement will occur.

In the embodiment shown the embedded electrical circuit 106 includes a charge controller 414. The charge controller 414 is connected to receive induced current from the induction coil 120 when the coil is disposed within an externally generated magnetic field, such as would be produced by the charging apparatus 300 shown in FIG. 3. The induced current is received as an alternating current and converted into a regulated direct current suitable for charging the energy source 118. The charge controller 414 is in communication with the microprocessor 400, which receives status information indicating a state of charge of the battery and/or whether an induced current is currently being received by the induction coil 120. The status information may be relayed via a Bluetooth transmission to the host computing platform 408 to alert an operator of the host computing platform of the current status of the movement sensing apparatus 100, such as the state of charge of the energy source 118.

In the movement sensing apparatus embodiment shown in FIGS. 1 and 4, the movement sensor 102 is located on the embedded electrical circuit 106 while the movement sensors 108 and 110 are connected to the board via the flexible interconnect 122. Additional movement sensors 418 at other locations on the insole 104 may also be included. In one embodiment the sensors 102, 108 and 110 are configured to transmit movement data to the to the processor circuit 112 via a Serial Peripheral Interface bus (SPI), which allows the different sensors to share data lines while a single chip select line specific to each movement sensor is required. When the chip select line for a particular movement sensor is asserted by the microprocessor 400, data may be transferred from the sensor to the microprocessor via the SPI bus. The SPI interface provides a robust high speed interface for communicating movement data between the movement sensors 102, 108 and 110 and the microprocessor 400. The processor circuit 112 may also be configured to make use of direct memory access (DMA) by configuring the sensors 102, 008, and 110 to directly access the RAM 406 for storing movement data, thus increasing the rate at which data can be captured by the processor circuit 112. Rapid data capture and transfer within the movement sensing apparatus 100 and to the host computing platform 408 has the advantage of making apparatus capable of generating real-time data for real-time or near real-time movement analysis.

Figure 5:
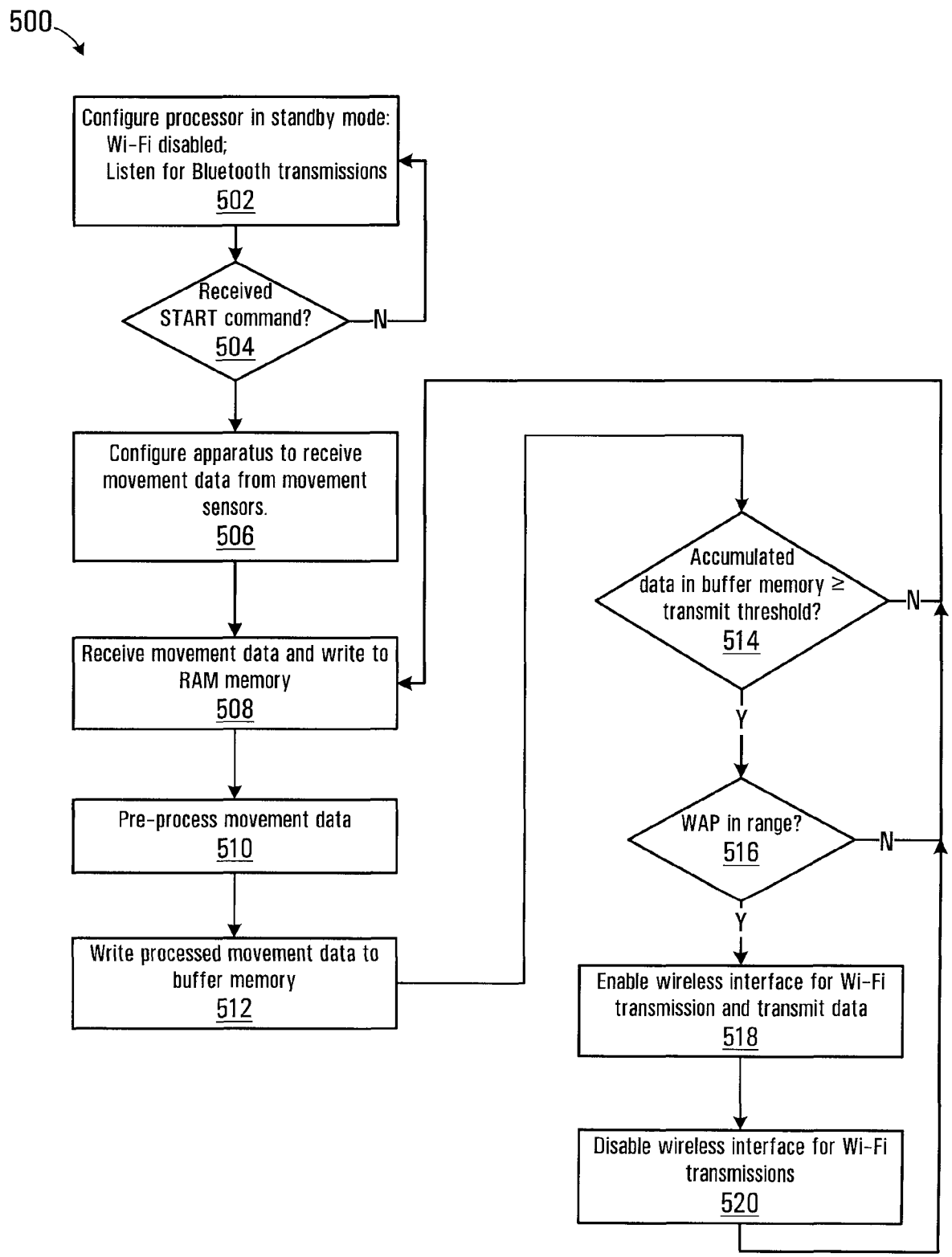
FIG. 5 is a process flowchart depicting blocks of code for directing a processor circuit of the movement sensing apparatus shown in FIG. 4 to carry out a movement test.

Referring to FIG. 5, a flowchart depicting blocks of code for directing the processor circuit 112 to perform a movement test is shown generally at 500. The blocks generally represent program codes that may be read from the ROM 404 for directing the microprocessor 400 to perform various testing functions. The actual code to implement each block may be written in any suitable program language, such as C, C++, C #, Java, and/or assembly code, for example.

The process 500 begins at block 502, which directs the microprocessor 400 to configure the movement sensing apparatus 100 in standby mode. This may involve disabling Wi-Fi functions of the wireless interface to inhibit transmission and conserve energy in the energy source 118 while continuing to listen for Bluetooth transmissions. IEEE 802.11 Wi-Fi connections will drain considerably more power from the energy source 118 than a Bluetooth connection. The microprocessor 400 may further be directed by block 502 to implement other power saving features provided by the various components of the movement sensing apparatus 100. Operational data and commands may thus be transmitted between the host computing platform 408 and the movement sensing apparatus 100 using the more energy efficient Bluetooth transmission protocol. The other operational data may include status data representing a status of the movement sensing apparatus 100 transmitted to the host computing platform. Program codes may also be downloaded from the host computing platform 408 via the Bluetooth protocol to the wireless interface 402 and written by the microprocessor 400 to ROM 404 for configuring the movement sensing apparatus 100 for movement test functionality. Since the ROM 404 only has a limited capacity, programming via Bluetooth is a viable protocol for downloading codes to the movement sensing apparatus 100 and has the advantage of conserving energy.

Block 504 then directs the microprocessor 400 to determine whether a START command has been received from the host computing platform 408. In other embodiments, the START command may be received from a device such as a smartphone via Bluetooth or other wireless transmission protocol. In some embodiments, the movement sensors 102, 108 and 110 may be capable of signaling the microprocessor 400 when movement of the insole 104 is detected. In this case the microprocessor 400 may initially be held in a low-power consumption standby state until signaling by the sensors in response to movement causes the microprocessor to come out of the standby state, thus acting as the START command. Similarly, if no movement is detected for a period of time, the microprocessor 400 may suspend operations and revert to the standby state.

If the START command has been received, the process continues at block 506 where the movement sensing apparatus 100 is configured to receive movement data from the movement sensors 102, 108 and 110. The microprocessor 400 is then directed to block 508. If at block 504 the START command has not yet been received, the microprocessor 400 is directed back to block 502 and the movement sensing apparatus 100 remains in standby mode.

Block 508 directs the microprocessor 400 to receive movement data from the sensors 102, 108 and 110 and to write the data to the RAM 406. The movement data is streamed from each sensor into the RAM 406 and may be uniquely associated with the particular sensor, for example the heel sensor 110, toe sensor 108 or mid-foot sensor 102. The microprocessor 400 transfers movement data from each one of the movement sensors 102, 108 and 110 by asserting the chip select line for the sensor and thus movement data received at the microprocessor can be identified based on a particular originating sensor.

In one embodiment, movement data may be generated by each of the sensors 102, 108 and 110 at a rate of between about 250 and 1000 samples or more per second and each sample consists of multiple bits. It may also be desirable to provide continuous monitoring of the test subject's movements during a movement test, thus generating a significant amount of data on an ongoing basis. Data received from the three or more sensors may thus rapidly overwhelm the transmission capacity if the transmitted using the Bluetooth function of the wireless interface 402. In contrast the IEEE 802.11 Wi-Fi transmission is capable of a bandwidth typically an order of magnitude higher than Bluetooth. Transmission via Wi-Fi would thus be generally necessary for any applications where there are several sensors in the movement sensing apparatus 100 and/or the desired rate of movement data capture rate is high. Bluetooth protocol transmissions may only be practical for the least demanding movement test applications.

Block 510 then directs the microprocessor 400 to pre-process the movement data. In one embodiment the pre-processing may involve compression of the data using an algorithm such as delta encoding/compression to facilitate more efficient transmission over the wireless interface. Alternatively or additionally the pre-processing may involve encrypting the data prior to transmission. An encryption algorithm such as a secure has algorithm (SHA) involving an asymmetrical encryption key exchanged between the movement sensing apparatus 100 and the host computing platform 408 may be employed. Encryption of the data has the advantage of preventing unauthorized access to the movement data, which may be desirable in cases where the test subject is a professional athlete, for example. In some embodiments the pre-processing may involve other processing of the movement data, such as filtering, selection of a subset of the data for later transmission, or other processing functions.

Following pre-processing at block 510, block 512 directs the microprocessor 400 to write the pre-processed movement data to the buffer memory 114. Block 514 then directs the microprocessor 400 to determine whether the amount of data accumulated in the buffer memory has reached a transmission threshold. In one embodiment the transmission threshold is set at a data size or proportion of the total capacity of the buffer memory 114 for efficient burst transmission via the wireless interface 402. For example, the transmission threshold may be pre-determined based on a fixed proportion of the total capacity of the buffer memory 114. If at block 514, the transmission threshold has not yet been reached, the microprocessor 400 is directed back to block 508 and the further movement data is received.

If at block 514, the transmission threshold has been reached, the process continues at block 516, which directs the microprocessor 400 to determine whether any of the wireless access points 410 and 412 are in wireless transmission range. If no wireless access point is currently in range, block 516 directs the microprocessor 400 back to block 508 and further movement data is accumulated and written to the buffer memory 114. In embodiments where there is some likelihood that none of the wireless access points will be in range for a period of time, the transmission threshold may be set at a lower proportion of the total capacity of the buffer memory 114 to ensure that sufficient capacity remains for accumulating movement data until a wireless access point is again in range. By uploading movement data more frequently, the amount of buffer memory 114 available for storing data may be maximized to allow for periods when no access point is in range. In some embodiments the transmission threshold may be dynamically changed by the microprocessor 400 during the movement test based on the availability of Wi-Fi connections and other conditions.

If at block 516, one of the wireless access points 410 and 412 is in range, the microprocessor is directed to block 518 where the microprocessor is directed to enable the wireless interface 402 for Wi-Fi transmission and to perform the burst transmission of the movement data accumulated in the buffer memory 114. Block 520 then directs the microprocessor 400 to again disable the wireless interface 402 for Wi-Fi transmissions, thus conserving energy while further movement data is accumulated and written to the buffer memory 114. The processor circuit 112 is thus operably configured to inhibit transmission by the wireless interface 402 while accumulating movement data in the buffer memory 114, and to transmit movement data from the buffer memory to the host computing platform 408 in a burst transmission when the accumulated movement data in the buffer memory reaches the transmission threshold.

In some embodiments the buffer memory 114 may be configured to have sufficient capacity to accumulate movement data for a period of time spanning an entire movement test, in which case the transmission threshold may be set at or near a total capacity of the buffer memory and the movement data may be subsequently transferred to the host computing platform 408 in a single burst transmission on conclusion of the movement test. Buffering of the movement data in the buffer memory 114 has several other advantages. For example, if the energy source 118 becomes depleted and is unable to power the embedded electrical circuit 106 to complete a movement test, the buffering facilitates recovery of test data up to the capacity of the buffer memory 114. Alternatively, when one of the movement sensors 102, 108 and 110 detect movement of the movement sensing apparatus 100 and cause the microprocessor 400 to come out of the standby state, the process 500 may be automatically initiated for recording movement data. If none of the wireless access points 410 and 412 are in range, the movement data would be written to the buffer memory 114 for later uploading to a host computing platform.

When implemented on the processor circuit 112, the process 500 effectively reduces the energy consumption due to energy intensive processes like the Wi-Fi transmission that consume a greater proportion of the stored energy thus facilitating a longer movement test duration on a single charge of the energy source 118.

Figure 6:
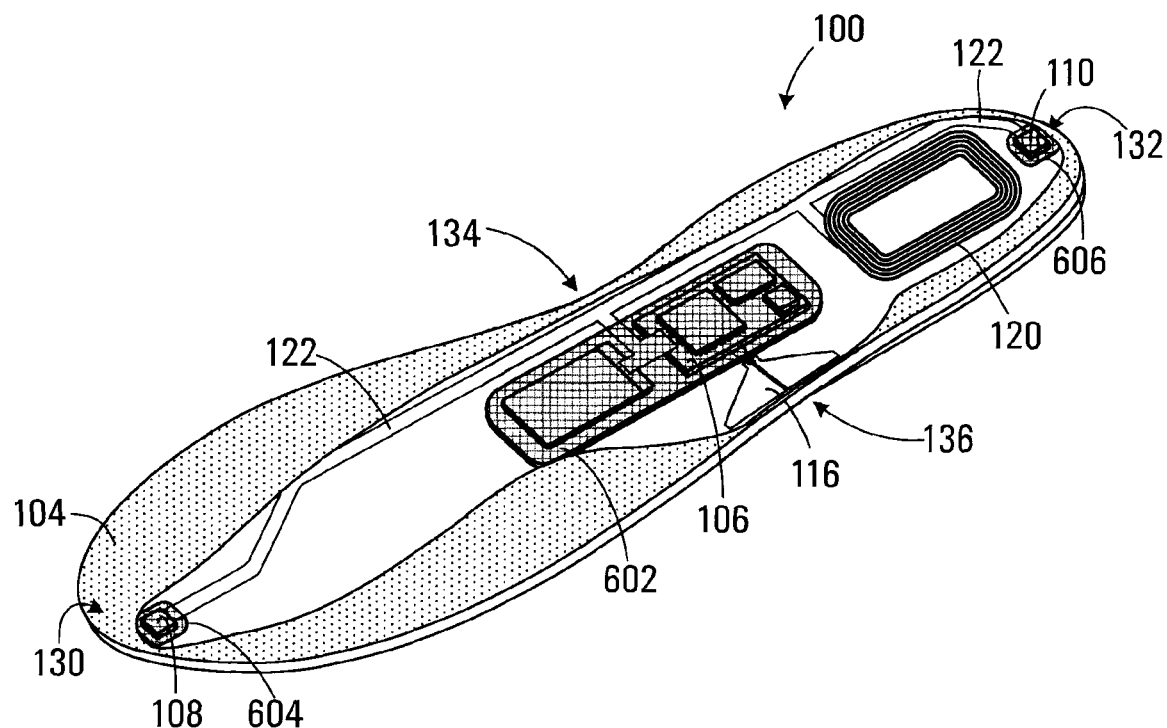
FIG. 6 is a perspective view of a movement sensing apparatus in accordance with another disclosed embodiment.

A further embodiment of a movement sensing apparatus is shown at 600 in FIG. 6. Referring to FIG. 6, the movement sensing apparatus 600 includes the embedded electrical circuit 106, energy source 118, flexible interconnect 122, induction coil 120, and movement sensors 108 and 110 as generally described above in connection with the movement sensing apparatus 100 of FIG. 1. However, in this embodiment the insole 104 further includes a strain plate 602 disposed over the embedded electrical circuit and the energy source 118. Further strain plates 604 and 608 are optionally disposed over the respective movement sensors 108 and 110. The strain plates 602, 604, and 606 redirect forces exerted by the test subject's foot away from the underlying components. In the embodiment shown the strain plate 602 covers both the embedded electrical circuit 106 and the energy source 118, but in other embodiments these components may be protected by separate strain plates (not shown). While the most sensitive electrical components such as the embedded electrical circuit 106 and energy source 118 are placed in the instep region of the insole to avoid high contact pressures being exerted on these components, additional protection in the form of the strain plates may further protect and extend the service life of the movement sensing apparatus 100.

Figure 7:
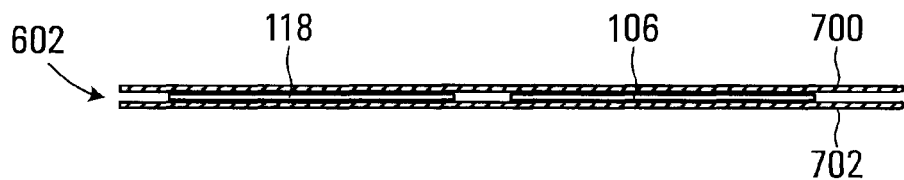
FIG. 7 is a cross sectional view of an embedded electrical circuit, energy source, and strain plate for one disclosed embodiment associated with the movement sensing apparatus shown in FIG. 6.

Referring to FIG. 7, in one embodiment the strain plate 602 may include an upper plate 700 disposed above the embedded electrical circuit 106 and energy source 118 and a lower plate 702 disposed below these components of the movement sensing apparatus 100. The movement sensors 108 and 110 may be similarly protected by upper and lower strain plates.

Figure 8:
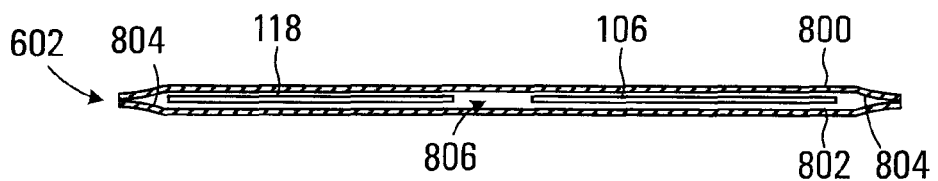
FIG. 8 is a cross sectional view through the embedded electrical circuit, energy source, and strain plate for another disclosed embodiment associated with the movement sensing apparatus shown in FIG. 6.

Referring to FIG. 8, in another embodiment an upper strain plate 800 and lower strain plate 802 are provided as shown in FIG. 7. However in this embodiment the strain plates each include a concave inner surface such that the upper and lower plates 800 and 802 engage at their respective peripheral edges providing an interior volume 806 for accommodating the embedded electrical circuit 106 and/or energy source 118 such that forces imparted on the at least one of the upper and lower plates by the test subject's foot are redirected to the peripheral edge. Alternatively, only one of the upper strain plate 800 and lower strain plate 802 may have the concave inner surface while the other strain plate has a planar configuration. The strain plates associated with the movement sensors 108 and 110 may be similarly configured.

In one embodiment the strain plates 602, 604, 606, 700, 702, 800 and 802 may be fabricated from a relatively thin composite material such as carbon fiber. In one embodiment a carbon fiber strain plate may have a thickness of about 0.7 mm. Alternatively, one or more of the strain plates may be fabricated from steel or another rigid or semi-rigid material.

The above disclosed embodiments of the movement sensing apparatus 100 provide both structural and operational advantages whether the apparatus implemented in an insole, such as shown in FIG. 1 or within another portion of the footwear. The disclosed embodiments provide for efficient use of energy within the apparatus thus extending the operating time and also permit operation over a wide area without impacting the test subject's comfort or motion.

While specific embodiments have been described and illustrated, such embodiments should be considered illustrative only and not as limiting the disclosed embodiments as construed in accordance with the accompanying claims.

What is claimed is:

1. A movement sensing apparatus for use in a footwear item, the apparatus comprising:
    at least one movement sensor operable to generate movement signals representing movement of the footwear item while being worn on a test subject's foot;
    an embedded electrical circuit including:
        a processor circuit coupled to receive the movement signals from the at least one movement sensor;
        a buffer memory in communication with the processor circuit for storing movement data representing the movement signals;
        a wireless interface controlled by the processor circuit an operably configured to wirelessly transmit movement data to an external host computing platform via an antenna;
    an energy source operable to provide operating power to the embedded electrical circuit and movement sensor; and
    wherein the processor circuit is operably configured to:
    inhibit transmission by the wireless interface while accumulating movement data in the buffer, memory;
    limit the storage of movement data in the buffer memory up to a customizable transmission threshold;
    transmit movement data from the buffer memory to the host computing platform in a burst transmission when the accumulated movement data in the buffer memory reaches the transmission threshold and when there is a wireless access point in range; and
    store movement data in buffer memory past the transmission threshold when there is no wireless access point in range.

2. The apparatus of claim 1 wherein the wireless interface is operably configured to implement an IEEE 802.11 transmission protocol.

3. The apparatus of claim 2 wherein the wireless interface is further operably configured to implement a Bluetooth transmission protocol and wherein: the burst transmission is transmitted to the host computing platform using the IEEE 802.11 transmission protocol; and other operational data is transmitted between the host, computing platform and the movement sensing apparatus using the Bluetooth transmission protocol.

4. The apparatus of claim 3 wherein the other operational data comprises at least one of:

commands issued by the host computing platform to the movement sensing apparatus;

status data representing a state of the movement sensing apparatus transmitted to the host computing platform; and program codes downloaded from the host computing platform to a program memory in communication with the processor circuit for configuring movement test functionality of the movement sensing apparatus.

5. The apparatus of claim 1 wherein the antenna is disposed under a lateral instep portion of the test subject's foot.

6. The apparatus of claim 1 wherein the embedded electrical circuit is disposed below an instep portion of the test subject's foot.

7. The apparatus of claim 1 wherein the energy storage element is disposed below an instep portion of the test subject's foot.

8. The apparatus of claim 1 further comprising a strain plate disposed over at least one of the embedded electrical circuit, the movement sensor, and the energy source and wherein the strain plate is operably configured to redirect forces exerted by the test subject's foot away from the embedded electrical circuit, movement sensor, or the energy source.

9. The apparatus of claim 8 wherein the strain plate is operably configured to cover both the embedded electrical circuit and the energy source.

10. The apparatus of claim 8 wherein each strain plate comprises an upper plate disposed above the at least one of the embedded electrical circuit, the movement sensor, and the energy source and a lower plate disposed below the at least one of the embedded electrical circuit, the movement sensor, and the energy source.

11. The apparatus of claim 10 wherein at least one of the upper and lower plates includes a concave inner surface and wherein the upper and lower plates are operably configured to engage at a peripheral edge providing an interior volume for accommodating the at least one of the embedded electrical circuit, the movement sensor, and the energy source such that forces imparted on the at least one of the upper and lower plates by the test subject's foot are redirected to the peripheral edge.

12. The apparatus of claim 8 wherein the strain plate comprises one of a carbon fiber plate and a steel plate.

13. The apparatus of claim 12 wherein the strain plate has a thickness of about 0.7 mm.

14. The apparatus of claim 1 wherein the movement sensor comprises a plurality of inertial movement sensors, at least one sensor being located in a heel region of the footwear item and at least one sensor being located in a toe region of the footwear item, each sensor being connected to the processor circuit via a flexible and stretchable interconnect.

15. The apparatus of claim 14 wherein the movement sensor apparatus is accommodated on a flexible substrate and wherein the flexible interconnect comprises a conductive material printed onto the flexible substrate.

16. The apparatus of claim 1 wherein the energy source comprises a battery capable of dynamically flexing in response to movement of the test subject's foot.

17. The apparatus of claim 1 further comprising an, induction coil operably configured to receive an externally applied alternating magnetic field and to generate a charging current for charging the energy source.

18. The apparatus of claim 1 further comprising a host computing platform operably configured to receive the burst transmission of movement data from the movement sensing apparatus.

19. The apparatus of claim 18 wherein the host computing platform comprises a plurality of wireless access points spaced apart within a test region and being operable to receive the burst transmission.

20. The apparatus of claim 19 wherein the movement sensing apparatus is further configured to transmit movement data from the buffer memory to the host computing platform in a burst transmission when the movement sensing apparatus is in wireless transmission range of one of the plurality of wireless access points.

21. The apparatus of claim 1 wherein the movement sensing apparatus is embedded within a removable insole inserted into the footwear item.

22. The apparatus of claim 1 wherein the processor circuit is operably configured to pre-process the movement data prior to storing the movement data in the buffer memory, wherein the pre-processing comprises at least one of compressing the data and encrypting the data.

* * * * *